US011542562B2

(12) United States Patent
Ma et al.

(10) Patent No.: US 11,542,562 B2
(45) Date of Patent: Jan. 3, 2023

(54) SINGLE NUCLEOTIDE POLYMORPHISM MARKER RELATED TO CHINESE HORSE SHORT STATURE TRAIT AND USE THEREOF

(71) Applicant: INSTITUTE OF ANIMAL SCIENCES OF CHINESE ACADEMY OF AGRICULTURAL SCIENCES, Beijing (CN)

(72) Inventors: Yuehui Ma, Beijing (CN); Lin Jiang, Beijing (CN); Xuexue Liu, Beijing (CN); Yabin Pu, Beijing (CN); Yanli Zhang, Beijing (CN)

(73) Assignee: INSTITUTE OF ANIMAL SCIENCES OF CHINESE ACADEMY OF AGRICULTURAL SCIENCES, Beijing (CN)

( * ) Notice: Subject to any disclaimer, the term of this patent is extended or adjusted under 35 U.S.C. 154(b) by 159 days.

(21) Appl. No.: 17/010,539

(22) Filed: Sep. 2, 2020

(65) Prior Publication Data
US 2021/0071271 A1 Mar. 11, 2021

(30) Foreign Application Priority Data
Sep. 6, 2019 (CN) .......................... 201910842289.4

(51) Int. Cl.
*C12Q 1/68* (2018.01)
*C12Q 1/6895* (2018.01)
*C12Q 1/6837* (2018.01)

(52) U.S. Cl.
CPC .......... *C12Q 1/6895* (2013.01); *C12Q 1/6837* (2013.01); *C12Q 2600/13* (2013.01); *C12Q 2600/156* (2013.01); *C12Q 2600/16* (2013.01)

(58) Field of Classification Search
CPC C12Q 1/6895; C12Q 1/6837; C12Q 2600/13; C12Q 2600/156; C12Q 2600/16
See application file for complete search history.

(56) References Cited

FOREIGN PATENT DOCUMENTS

| CN | 105713982 A | * | 6/2016 |
| CN | 108410866 A | * | 8/2018 |
| CN | 110541041 A | * | 12/2019 |

OTHER PUBLICATIONS

Semagn, K., Babu, R., Hearne, S. and Olsen, M., 2014. Single nucleotide polymorphism genotyping using Kompetitive Allele Specific PCR (KASP): overview of the technology and its application in crop improvement. Molecular breeding, 33(1), pp. 1-14. (Year: 2012).*
Kader et al., 2016. Identification of copy number variations in three Chinese horse breeds using 70Ksingle nucleotide polymorphism BeadChip array. Animal genetics, 47(5), pp. 560-569. (Year: 2016).*
Liu et al., 2018. Detecting selection signatures on the X chromosome of the Chinese Debao pony. Journal of animal Breeding and Genetics, 135(1), pp. 84-92. (Year: 2018).*
Liu et al., 2022. Asingle-nucleotide mutation within the TBX3 enhancer increased body size in Chinese horses. Current Biology, 32(2), pp. 480-487. (Year: 2022).*
English translation of CN105713982A pub. Jun. 29, 2016 by Ma et al., recovered from espascenet.com. (Year: 2016).*
English translation of CN108410866A pub. Aug. 17, 2018 by Jian g et al., recovered from espacenet.com (Year: 2018).*
English translation of CN110541041A pub. Dec. 6, 2019 by Jian g et al., recovered from espascenet.com (Year: 2019).*
KASP genotyping chemistry User guide and manual, pub. by LGC Genomics, 2013, recovered from www.lgcgenomics.com. (Year: 2013).*

* cited by examiner

*Primary Examiner* — Gary Benzion
*Assistant Examiner* — Olayinka A Oyeyemi
(74) *Attorney, Agent, or Firm* — Flener IP & Business Law; Zareefa B. Flener

(57) ABSTRACT

The invention relates to a single nucleotide polymorphism (SNP) marker related to a Chinese horse short stature trait. The SNP molecular marker is located at the 501$^{th}$ position of a sequence shown in SEQ ID NO.1, polymorphism is G/A, and the SNP marker corresponds to base pair 18,205,998 on chromosome 8 in a horse. The SNP marker related to the Chinese horse short stature trait and use thereof provided by the present invention have the following advantages that: (1) the molecular marker is not restricted by the age, sex and the like of Chinese horses, is used in early breeding of the Chinese horses, performs accurate screening immediately at birth, and significantly promotes the breeding process of dominant pony varieties of the Chinese horse; (2) a method for detecting SNP of a Chinese horse TBX3 gene is accurate, reliable, and easy to operate.

5 Claims, 1 Drawing Sheet
Specification includes a Sequence Listing.

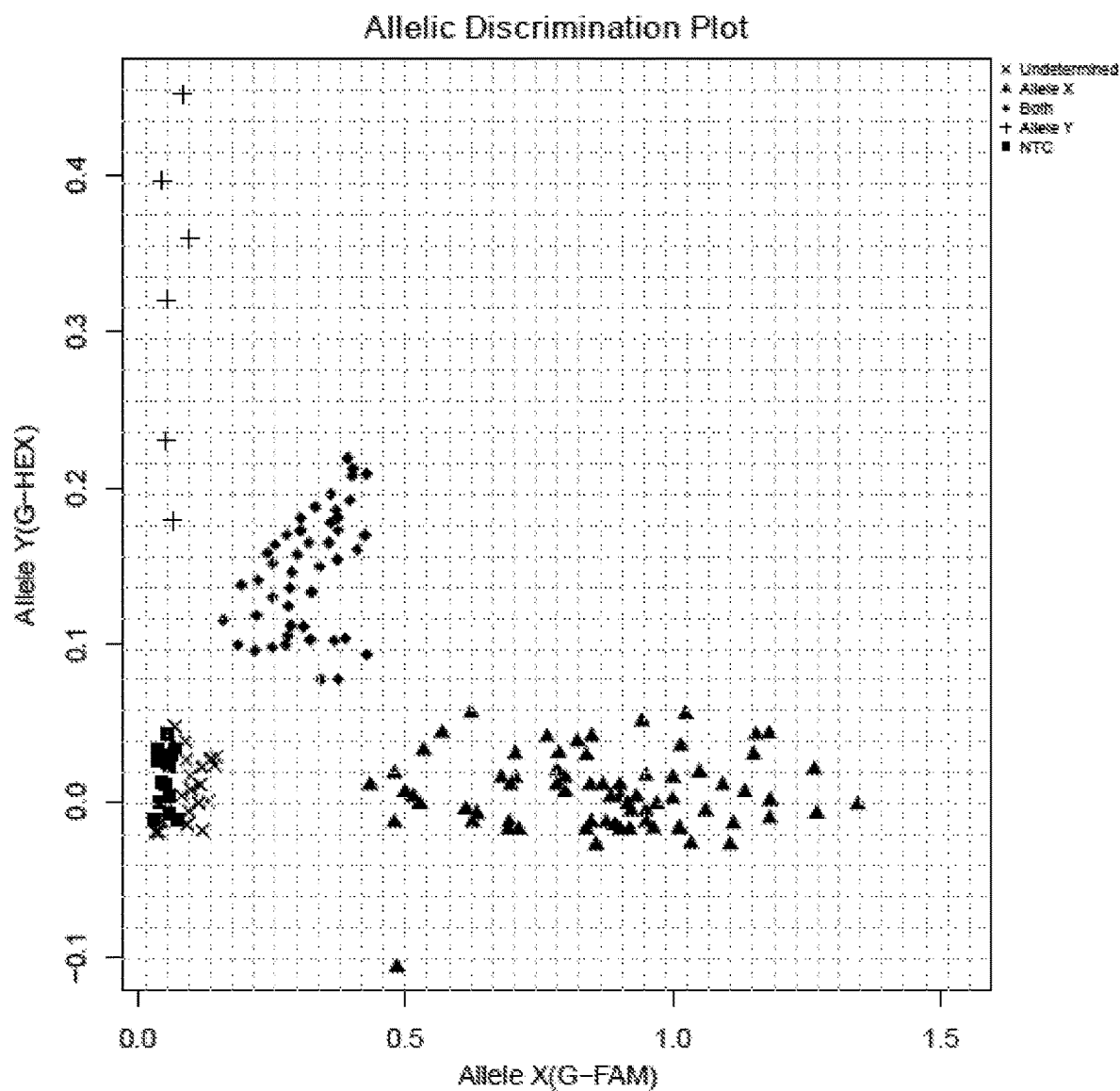

SEQUENCE LISTING

<160> NUMBER OF SEQ ID NOS: 4

<210> SEQ ID NO 1
<211> LENGTH: 1001
<212> TYPE: DNA
<213> ORGANISM: artificial sequence

```
<220> FEATURE:
<223> OTHER INFORMATION: a sequence where the SNP marker is located

<400> SEQUENCE: 1
cctctcgaat cccaaatgtg gatccttctc ccgcgcgtaa agcagcgtct gtcggactct      60
gcccaggggc aggctcatcc gctgtttcct gcctgtcttt tgtacagcga gaagcgggga    120
gagagaagat agaggggatc tgcgaagagg aaaaaaaaaa aaaaaagacc gtgtagagcc    180
cgcggctgga gactaaagcc ctggcctgga gcgcgcaagc cttgtgggtt cccgcggcgg    240
ccaggcctgg cacaagtctt cagaacacgc tagccaatgt ttaactcgca tgcagtggcc    300
accaggccgc ttttgtttgt tcgcaaatta atcacccagc gcacggccgg cgccagagtg    360
ggtttatcac ccaccgggag gggggcgcgg cggcctagca gagacaaaga ggagttcgca    420
cctttccgct tttgatccca agttaccgcg gcctccctgc ataatacgag tctcctgggg    480
ccgagtctgg gaggtcagtc gtaattggcg gaagtttgca gaccattagc aagatgtcga    540
cattttcgat tcagaacccc gcaaactttc ctctcccccg cctccttgcg cgctggagta    600
ggagtgaggg tcaagagtgg caactggggt gaccccaggg ttaagtcaga actacgggca    660 aaataggcg catagggacg aggggcagt gtgaggggca gaaatcacgc tcagtccacg      720
gtggggccaa aggcgagtgg acgtatttac aagtacagta aaatcagcga gcctcccttc    780
cgtgtcctaa acaaaaggga gggcacaatg cagaggcgcg agtaaaacgt ctctctccag    840
cgcgtctgga tgcttgggc accgagtggg tgaggagggg gtcagtcaca ctgtggttac     900
agaattactt cgcttccact cggagcggcg tggcagagac tggcggcgac tgcaggcaaa    960
accaggtcgc cgggtttggg gccgctcctg aaagcgcagc g                       1001

<210> SEQ ID NO 2
<211> LENGTH: 21
<212> TYPE: DNA
<213> ORGANISM: artificial sequence
<220> FEATURE:
<223> OTHER INFORMATION: primer 1

<400> SEQUENCE: 2
ccgagtctgg gaggtcagtc g                                               21

<210> SEQ ID NO 3
<211> LENGTH: 21
<212> TYPE: DNA
<213> ORGANISM: artificial sequence
<220> FEATURE:
<223> OTHER INFORMATION: primer 2

<400> SEQUENCE: 3
ccgagtctgg gaggtcagtc a                                               21

<210> SEQ ID NO 4
<211> LENGTH: 22
<212> TYPE: DNA
<213> ORGANISM: artificial sequence
<220> FEATURE:
<223> OTHER INFORMATION: primer 3

<400> SEQUENCE: 4
gtctgcaaac ttccgccaat ta                                              22
```

SINGLE NUCLEOTIDE POLYMORPHISM MARKER RELATED TO CHINESE HORSE SHORT STATURE TRAIT AND USE THEREOF

TECHNICAL FIELD

The present invention relates to the field of genetics, and in particular to a single nucleotide polymorphism (SNP) marker related to the short stature trait of a Chinese horse breed and use thereof.

BACKGROUND

SNP locus principally refers to polymorphism of deoxyribonucleic acid (DNA) fragments caused by a single deoxyribonucleotide mutation in a genomic DNA sequence. SNP merely relates to single base variation, including replacement, insertion, and deletion.

So far, the commonly used SNP detection methods include Sanger sequencing, DNA microarray, time-of-flight mass spectrometry (TOF-MS), and the latest next generation sequencing (NGS). SNP, as a genetic marker, has been widely used in research fields of gene mapping, cloning, genetic breeding, genetic diversity analysis, etc.

T-Box transcription factor 3 (TBX3) is one of the key genes for regulating growth and development, which is widely present in embryonic tissues and plays an important role in the development of embryonic stem cells and cardiac conduction system. Deletion or mutation of this gene thereof causes human ulnar-mammary syndrome. Genome-wide association study and genome-wide selective signal screening of Debao ponies, Yili horses, and Mongolian horses in China found that one polymorphic variation at TBX3 locus has a significant effect on the body size of Chinese horses.

Ponies are short, nimble, good-tempered, and particularly suitable for junior equestrian teaching. With the rapid development of junior equestrian clubs throughout China, ponies have an immeasurable economic prospect in the culture and education industry. So far, however, all equestrian clubs in China depend on the imported ponies, and it costs RMB 50,000 to introduce a pony. Nevertheless, due to the lack of breeding markers, molecular breeding technique and utilization efficiency, the Chinese pony resource superiority cannot be translated into an economic advantage. Currently, HMGA2 identified by genome-wide scan influenced the body size of pony breeds overseas, but previous research indicated that ponies in China and abroad had independent evolution histories. Therefore, it is necessary to develop a Chinese pony-specific molecular marker for Chinese pony breeding.

SUMMARY

A first objective of the present invention is to provide an SNP marker for the assisted identification of Chinese horse short stature trait, and use thereof.

A second objective of the present invention is to primers for detecting the SNP marker related to the Chinese horse short stature trait and a kit including the primers.

In order to achieve the first objective of the present invention, the present invention provides an SNP marker related to a Chinese horse short stature trait, where the SNP marker is located at base pair 18,205,998 on chromosome 8 in a horse (gi 194246389:18205498-18206498 Equus caballus isolate Twilight breed thoroughbred chromosome 8, EquCab2.0, whole genome shotgun sequence).

The inventors have carried out a great deal of research on association between genotype and height phenotype in Chinese horse varieties from different regions, and have found that the SNP locus provided by the present invention is significantly associated with horse height (chi-square test, P<2.2e-16). Allele A has a frequency of 64.07% in ponies, while allele G has a frequency of 82.14% in ordinary horses. AA genotype has a frequency of 65.95% in ponies and 17.85% in ordinary horses; the average height of horses with AA genotype is significantly shorter than those with GG genotype (chi-square test, P<2.2e-16). This is of great significance to genotyping and screening Chinese horses with short stature trait. When the genotype of a Chinese horse is AA, the horse is determined to have a short stature trait; when the genotype of a Chinese horse is GG, the horse is determined to have a tall stature trait. This increases the accuracy and efficiency of horse height screening.

In the present invention, definition of pony height is the same as that accepted internationally, i.e., a horse with a horseback height of <106 cm is defined as a pony, while that with a horseback height of >106 cm is defined as a high horse.

The present invention further provides an SNP marker related to a Chinese horse short stature trait, where the SNP marker is located at the 501$^{th}$ position of a sequence shown in SEQ ID NO.1, polymorphism is G/A, and corresponds to base pair 18,205,998 on chromosome 8 in a horse.

The SNP marker of the present invention is amplified by the following primers:

primer 1: CCGAGTCTGGGAGGTCAGTCG (SEQ ID NO. 2);

primer 2: CCGAGTCTGGGAGGTCAGTCA (SEQ ID NO. 3); and primer 3: GTCTGCAAACTTCCGCCAATTA (SEQ ID NO. 4); where, when in use, primers 1 and 2 label fluorophores with different colors, respectively.

The present invention further provides a specific primer combination for detecting the SNP marker of the present invention, including:

```
primer 1:
                                    (SEQ ID NO. 2)
CCGAGTCTGGGAGGTCAGTCG;

primer 2:
                                    (SEQ ID NO. 3)
CCGAGTCTGGGAGGTCAGTCA;
and primer 3:
                                    (SEQ ID NO. 4)
GTCTGCAAACTTCCGCCAATTA.
```

A kit or reagent including the specific primer combination falls into the protection scope of the present invention.

The present invention provides use of the SNP marker, the specific primer combination, or the kit or reagent including the specific primer combination in identifying pony varieties of Chinese horse.

The present invention provides use of the SNP marker, the specific primer combination, or the kit or reagent including the specific primer combination in molecular marker-assisted breeding of Chinese horses.

The present invention provides use of the SNP marker, the specific primer combination, or the kit or reagent including the specific primer combination in the improvement of germplasm resources of Chinese horses.

The present invention provides use of the SNP marker, the specific primer combination, or the kit or reagent including the specific primer combination in research on taxonomy and breeding of Chinese horses.

Use of the SNP marker related to the Chinese horse short stature trait in molecular marker-assisted breeding of Chinese horses further falls into the protection scope of the present invention.

The present invention provides a method for identifying a Chinese horse with short stature trait, including the following steps:

1) extracting genomic DNA from a test horse;
2) using the genomic DNA of the test horse as a template to conduct polymerase chain reaction amplification with specific primers, to obtain a fragment of an amplified product; and
3) determining what type of a base is located at 501 bp in the fragment of the amplified product: if the base is A, then the test horse is determined to have a short stature trait; if the base is G, the test horse is determined to have a tall stature trait; namely, in the detection, an idiotype with fluorescence of primer 1 labeled groups is AA, and an idiotype with fluorescence of primer 2 labeled groups is GG.

Herein, the specific primers include:

```
primer 1:
                              (SEQ ID NO. 2)
CCGAGTCTGGGAGGTCAGTCG;

primer 2:
                              (SEQ ID NO. 3)
CCGAGTCTGGGAGGTCAGTCA;
and primer 3:
                              (SEQ ID NO. 4)
GTCTGCAAACTTCCGCCAATTA.
```

In the method of the present invention, in step 2), an amplification system used in the PCR (in 5 μl) includes: 2.43 μl of 50-100 ng/μl template DNA, 2.5 μl of KASP Master Mix, and 0.07 μl of KASP Assay Mix.

In the method of the present invention, in step 2), PCR conditions are as follows: step 1): 94° C. for 15 min; step 2): 10 cycles of 94° C. for 20 s and 61-55° C. for 1 min, with a 0.6° C. decrease in each cycle; and step 3): 26 cycles of 94° C. for 20 s and 55° C. for 1 min.

There is no particular restriction on methods for detecting the fragment of the PCR product, and detection methods conventional in the art may be used; preferably, genotypes of a test Chinese horse are detected by TOF-MS.

The SNP marker related to the Chinese horse short stature trait and use thereof provided by the present invention have the following advantages:

(1) The molecular marker is not restricted by the age, sex and the like of Chinese horses, is used in early breeding of the Chinese horses, performs accurate screening immediately at birth, and significantly promotes the breeding process of dominant pony varieties of the Chinese horse.

(2) A method for detecting an SNP of a Chinese horse TBX3 gene is accurate, reliable, and easy to operate.

(3) Detection of an SNP locus of the Chinese horse TBX3 gene provides scientific basis for Chinese horse height size marker assisted selection.

BRIEF DESCRIPTION OF THE DRAWINGS

FIG. 1 is a plot illustrating a cluster analysis of SNP typing of three genotypes by TOF-MS; herein, Allele Y axis represents an individual with GG genotype; Allele X axis represents an individual with AA genotype; Both represents an individual with AG genotype; and "X" represents an undetermined result of an individual.

DETAILED DESCRIPTION

The present invention will be described in detail below in combination with examples.

The following examples intend to illustrate the invention but not to limit the scope of the invention. Unless otherwise specified, technical means used in the examples are well known to those skilled in the art, and all raw materials used are commercially available.

Example 1 Identification of Loci of TBX3 Gene Polymorphism in Chinese Horses

1. Extraction of Genomic DNAs from Blood of Test Chinese Horses

Blood samples were collected from 210 ponies from Southwest China (including 19 from Debao, 34 from Bose, 35 from Wenshan, 20 from Yunnan, 15 from Lichuan, 32 from Jinjiang, 30 from Jianchang, and 25 from Guizhou), 308 horses with normal height (including 145 from Northwest China, 128 from Inner Mongolia, 24 from Northeast China, and 11 thoroughbred horses), and 11 Przewalski's horses. There were a total of 529 individuals from 21 populations. Genomic DNAs were extracted from the blood using a conventional method.

TABLE 1

Sample collection

| Variety | Abbreviation | Sampling site | Sample size | Type |
|---|---|---|---|---|
| Barkol horse | BLK | Barkol Kazakh Autonomous County, Xinjiang | 26 | Ordinary type |
| Heihe horse | HeHe | Huma County, Heilongjiang | 24 | Ordinary type |
| Kazakh horse | HSK | Xinyuan County, Xinjiang | 16 | Ordinary type |
| Mongolian horse | MoGo | Hulunbuir City, Inner Mongolia | 30 | Ordinary type |
| Sanhe horse | SaHe | Hulunbuir City, Inner Mongolia | 29 | Ordinary type |
| Abaga dark horse | SeSe | Xilin Gol League, Inner Mongolia | 34 | Ordinary type |
| Thoroughbred horse | ThB | The UK | 11 | Ordinary type |
| Wushen horse | WUS | Uxin Qi, Inner Mongolia | 27 | Ordinary type |
| Ujimqin horse | WuZh | Hulunbuir City, Inner Mongolia | 36 | Ordinary type |
| Xinihe horse | XNH | Hulunbuir City, Inner Mongolia | 35 | Ordinary type |
| Yili horse | YiLi | Zhaosu County, Xinjiang | 7 | Ordinary type |
| Yanqi horse | YaQi | Yanqi County, Xinjiang | 33 | Ordinary type |
| Yunnan pony | YuNa | Honghe Hani and Yi Autonomous Prefecture, Yunnan | 20 | Short stature type |
| Lichuan horse | LCH | Lichuan City, Hubei | 15 | Short stature type |
| Jinjiang horse | JiJi | Jinjiang County, Fujian | 32 | Short stature type |
| Baise horse | BaSe | Tianlin County, Guizhou | 34 | Short stature type |

TABLE 1-continued

Sample collection

| Variety | Abbreviation | Sampling site | Sample size | Type |
|---|---|---|---|---|
| Guizhou horse | GuZh | Bijie County, Guizhou | 25 | Short stature type |
| Debao pony | DeBa | Debao County, Guangxi | 19 | Short stature type |
| Jianchang horse | JiCh | Butuo County, Sichuan | 30 | Short stature type |
| Wenshan horse | WeSh | Wenshan County, Yunnan | 35 | Short stature type |
| Prewalski's horse | PrZ | Qitai County, Xinjiang | 11 | Wild horse |

2. Amplification of Nucleotide Fragments Containing SNP Locus

Primers were designed according to a sequence of TBX3 locus (gi 194246389:18100500-18101500 Equus caballus isolate Twilight breed thoroughbred chromosome 8, EquCab2.0, whole genome shotgun sequence) included in the National Center of Biotechnology Information (NCBI) database, including: primer 1: CCGAGTCTGGGAGGTCAGTCG (SEQ ID NO. 2), primer 2: CCGAGTCTGGGAGGTCAGTCA (SEQ ID NO. 3), and primer 3: GTCTGCAAACTTCCGCCAATTA (SEQ ID NO. 4).

A nucleotide fragment where the SNP to be detected was located was amplified with the genomic DNA in step 1.1 as a template, as shown in SEQ ID NO. 1. The SNP locus was located at 501 bp of a PCR amplified fragment, where bases were A or G.

Herein, an amplification system used in the PCR (in 5 µl) includes: 2.43 µl of 50-100 ng/µl template DNA, 2.50 µl of 2×KASP Master Mix, and 0.07 µl of KASP Assay Mix (mixed primer working solution).

Herein, in step 2), PCR conditions were as follows: step 1): 94° C. for 15 min; step 2): 10 cycles of 94° C. for 20 s and 61-55° C. for 1 min, with a 0.6° C. decrease in each cycle; and step 3): 26 cycles of 94° C. for 20 s and 55° C. for 1 min.

3. Detection of the PCR Amplified Fragment to Obtain an SNP Marker

A PCR product obtained in step 1.2 was sequenced. If a base at 501 bp of a sequence of the amplified product is A, then test Chinese horses belong to dominant pony varieties. FIG. 1 is a plot illustrating a cluster analysis of SNP typing of three genotypes by TOF-MS.

4. Genotyping

Test Chinese horses were genotyped by TOF-MS; genotypes of SNP loci in the test populations were determined according to TOF-MS results. Genotypes were divided into AA type, GG type, and AG type according to signal distribution positions of samples. Genotyping results of the three genotypes are shown in FIG. 1.

Example 2 Use in the Analysis and Detection of Associations Between Different Genotypes and Height Sizes of Chinese Horses A great deal of research on association between genotype and height phenotype in Chinese horse varieties from different regions was carried out in the present invention, and it was found that the SNP locus (which is located at the $501^{th}$ position of a sequence shown in SEQ ID NO.1, has a polymorphism of G/A, and corresponds to base pair 18,205,998 on chromosome 8 in a horse) provided by the present invention is significantly associated with horse height (chi-square test, $P<2.2e-16$). Allele A had a frequency of 64.07% in ponies, while allele G had a frequency of 82.14% in ordinary horses. AA genotype had a frequency of 65.95% in ponies and 17.85% in ordinary horses; the average height of horses with AA genotype was significantly shorter than those with GG genotype (chi-square test, $P<2.2e-16$). This was of great significance to genotyping and screening Chinese horses with short stature trait. When the genotype of a Chinese horse was AA, the horse was determined to have a short stature trait; when the genotype of a Chinese horse was GG, the horse was determined to have a tall stature trait. This increased the accuracy and efficiency of horse height screening.

Example 3

An expanded population analysis was conducted on loci of TBX3 gene polymorphism in 529 Chinese horses. In the SNP locus (which is located at the $501^{th}$ position of a sequence shown in SEQ ID NO.1, has a polymorphism of G/A, and corresponds to base pair 18,205,998 on chromosome 8 in a horse), the frequency of allele A was significantly higher in ponies than in other horses with ordinary height (not ponies) ($P<2.2e-16$). This further verified the association between the allele A at the SNP locus and Chinese horse short stature trait (as shown in Table 2).

TABLE 2

Numbers of genotypes at the SNP locus in Chinese ponies and ordinary horses

| Genotype | AA (horse) | AG (horse) | GG (horse) |
|---|---|---|---|
| Pony | 88 | 101 | 21 |
| Ordinary horse | 12 | 86 | 210 |

The present invention has been described in detail above with reference to general descriptions and particular embodiments, but it will be apparent to those skilled in the art that various modifications or variations can be made based on the present invention. Therefore, all these modifications or variations made without departing from the spirit of the invention fall within the scope of the invention.

What is claimed is:

1. A specific primer combination for detecting a single nucleotide polymorphism (SNP) marker related to a Chinese horse short stature trait, comprising:

```
                                      (SEQ ID NO: 2)
    primer 1: CCGAGTCTGGGAGGTCAGTCG;

(SEQ ID NO: 3)
    primer 2: CCGAGTCTGGGAGGTCAGTCA; and (SEQ ID NO: 4)
    primer 3: GTCTGCAAACTTCCGCCAATTA;
``` wherein the SNP marker is located at the $501^{st}$ position of SEQ ID NO: 1, wherein the polymorphism is G/A, and wherein SEQ ID NOS: 2-3 are each labeled with fluorophores of different colors.

2. A kit or reagent comprising the specific primer combination according to claim 1.

3. A method for identifying pony varieties of Chinese horse comprising a step of detecting a single nucleotide polymorphism (SNP) marker related to a Chinese horse short stature trait using a specific primer combination consisting of SEQ ID NOS: 2-4 and identifying pony varieties of Chinese horse from the single nucleotide polymorphism (SNP) marker.

4. The method according to claim 3, wherein the method for identifying pony varieties of Chinese horse comprises the following steps:
1) extracting genomic DNA from a test horse;
2) using the genomic DNA of the test horse as a template to conduct polymerase chain reaction (PCR) amplification with the specific primer combination comprising SEQ ID NOS: 2-4, to obtain amplified products; and
3) analyzing the amplified products to determine what type of a base is located at $501^{st}$ position of the amplified product having the nucleotide sequence consisting SEQ ID NO: 1 and wherein:
  if the base is A, then the test horse is determined to have a short stature trait;
  if the base is G, the test horse is determined to have a tall stature trait;
  wherein an idiotype with fluorescence of primer 1 labeled groups is AA, and
  wherein an idiotype with fluorescence of primer 2 labeled groups is GG;
  wherein SEQ ID NOS: 2-3 are each labeled with fluorophores of different colors.

5. The method according to claim 4 wherein, in step 2), wherein PCR conditions are as follows:
step 1): 94° C. for 15 min; after which step (2) is performed;
step 2): 10 cycles involving 94° C. for 20 s followed by an annealing for 1 min per each cycle, wherein the annealing temperature over 10 cycles is from 61-55° C., and the annealing temperature is reduced by a 0.6° C. decrease with each cycle; and following the completion of step (2), step (3) is performed;
wherein step 3): includes 26 cycles of denaturing and annealing at 94° C. for 20 s and 55° C. for 1 min per each cycle.

* * * * *